(12) United States Patent
Kepka et al.

(10) Patent No.: US 7,553,658 B2
(45) Date of Patent: Jun. 30, 2009

(54) RECOVERY OF PLASMIDS IN AN AQUEOUS TWO-PHASE SYSTEM

(75) Inventors: Cecilia Jansson Kepka, Bunkeflostrand (SE); Jenny Rhodin Edsö, Lund (SE); Folke Tjerneld, Limhamm (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 330 days.

(21) Appl. No.: 10/526,089

(22) PCT Filed: Jun. 17, 2003

(86) PCT No.: PCT/SE03/01016

§ 371 (c)(1),
(2), (4) Date: Feb. 23, 2005

(87) PCT Pub. No.: WO2004/020629

PCT Pub. Date: Mar. 11, 2004

(65) Prior Publication Data

US 2006/0166349 A1    Jul. 27, 2006

(30) Foreign Application Priority Data

Aug. 27, 2002    (SE) .................................. 0202552

(51) Int. Cl.
*C12N 1/08*     (2006.01)
*C12N 15/64*    (2006.01)
*C12N 15/10*    (2006.01)
(52) U.S. Cl. .................... 435/270; 435/91.4; 435/320.1
(58) Field of Classification Search ........................ None
See application file for complete search history.

(56) References Cited

U.S. PATENT DOCUMENTS 6,107,467 A * 8/2000 Ageland et al. ............. 530/359

FOREIGN PATENT DOCUMENTS

WO    WO98/11140    3/1998

OTHER PUBLICATIONS

Ohlsson R, (A rapid method for the isolation of circular DNA using an aqueous two-phase partition system. Nucleic Acids Res. Feb. 1978;5(2):583-90).*
Persson, J., et al., "Purification of protein and recycling of polymers in a new aqueous two-phase system using two thermoseparating polymers", *Journal of Chromatography A*, vol. 864, 1999, p. 31-48.
Tjerneld, F., et al., "Utilization of Temperature-induced Phase Separation for Purification of Biomolecules", *International Symposium on Separations for Biotechnology Reading: Separation for Biotechnology 3*. Cambridge: Royal Society of Chemistry, 1994, p. 505-511.
Ribeiro, S., et al., "Isolation of Plasmid DNA from Cell Lysates by Aqueous Two-Phase Systems", *Biotechnology and Bioengineering*, vol. 78, No. 4, May 2002, p. 376-384.

* cited by examiner

*Primary Examiner*—Michael Burkhart
(74) *Attorney, Agent, or Firm*—Yonggang Ji

(57) ABSTRACT

The present invention is a method for the purification of plasmid DNA comprising to provide a composition comprising a first polymer having inverse solubility characteristics and a second polymer immiscible in the first polymer; contacting said solution with an aqueous solution comprising plasmid DNA; providing phase separation and isolating the aqueous phase; and increasing the temperature of the isolated phase to a temperature above the cloud point of the first polymer and below the temperature where plasmid DNA is degraded and subsequently isolating the aqueous phase so formed. The invention also encompasses a kit for purification of plasmid DNA as described above.

7 Claims, 6 Drawing Sheets

RECOVERY OF PLASMIDS IN AN AQUEOUS TWO-PHASE SYSTEM

CROSS REFERENCE TO RELATED APPLICATIONS

This application is a filing under 35 U.S.C. §371 and claims priority to international patent application number PCT/SE2003/001016 filed Jun. 17, 2003, published on Mar. 11, 2004 as WO 2004/020629 and also claims priority to patent application number 0202552-6 filed in Sweden on Aug. 27, 2002; the disclosures of which are incorporated herein by reference in their entireties.

TECHNICAL FIELD

The present invention relates to a method for the purification of plasmid DNA in an aqueous two-phase system. The invention also encompasses a kit for purification of plasmid DNA from a cell lysate in an aqueous two-phase system. In addition, the present invention relates to the use of certain polymers in a two-phase system for the purification of plasmid DNA from a cell lysate.

BACKGROUND

One of the ways that genetic variability is maintained within a population is through recombination, a process involving the exchange of genetic information among different DNA molecules that results in a reshuffling of genes. To provide recombination in the field of genetic engineering, a vector is usually used. The most commonly used vector is the DNA plasmid, a small genetic element that permits microorganisms to store additional genetic information.

Plasmids are useful elements in many biotechnological applications these days. For example, in the medical and diagnostic fields, genetic engineering of cells is performed using plasmids that carry a gene encoding a protein, which is not expressed in the native cell.

Another use of plasmids as vectors is in the field of gene therapy, which is expected to be one of the fastest growing areas in the next decade. Gene therapy is a therapeutic strategy where nucleic acids are introduced to human cells to cure genetic defects e.g. cystic fibrosis. The first human gene therapy trials began in 1990, using an ex vivo strategy. In this approach, the patient cells are harvested and cultivated in the laboratory and then incubated with vectors to introduce the therapeutic genes. Even though approaches for delivering genes based on in vivo gene therapy, in which the virus is directly administered to the patients, have been suggested more recently as an alternative, the plasmid retains its importance in gene therapy.

Thus, the increased use of such biotechnological applications results in a need for large quantities of plasmid DNA. To this end, an efficient large-scale purification process, which can meet specifications in purity and quantitation, is required. Today, many purification methods are available for smaller molecules of sizes of about 10 nm, such as proteins. However, for the larger DNA plasmids, which are of sizes of 100 nm and above, much fewer purification methods are available.

Conventionally, the production of plasmid DNA involves fermentation, primary purification and high-resolution separation. Recently many methods have been suggested involving use of chromatography as the method for purification of plasmid DNA. However, the use of chromatography as a single purification technique alone for plasmid DNA involves several drawbacks, such as a slow diffusion, low capacity of the matrices, shearing of large plasmids and recovery of the plasmid in high salt concentration. Therefore, there is a need of a primary purification step before chromatography.

Use of a two-phase system has been suggested for purification of plasmid DNA. Aqueous two-phase systems are extremely mild and have shown a strong potential for use as a primary recovery step for plasmid purification. Plasmid DNA is today often produced in *Escherichia coli* and involves an alkaline lysis step for release of plasmid DNA from the bacterial cells. Several contaminants such as RNA, genomic DNA, proteins, cells and cells debris are released in the alkaline lysis step. Ribeiro et al. (S. C. Ribeiro et al: Isolation of Plasmid DNA from Cell Lysates by Aqueous Two-Phase Systems, 2002 Wiley Periodicals) has shown that plasmid DNA can be isolated in aqueous two-phase systems consisting of polyethylene glycol (PEG) and a salt. PEG is a linear polymer of ethylene oxide groups. The polymer is soluble in water, and at a certain salt concentration a two-phase system consisting of PEG and salt can be achieved. The PEG polymer can be removed by filtration or dialysis, which however often decreases the yield. Another drawback with this method is that PEG is a relatively expensive chemical, which will be of importance in large-scale processes. Furthermore, plasmid DNA resulting from this method will be present in an environment of high salt concentration, which is a disadvantage in applications such as gene therapy.

An alternative two-phase system differs from the PEG/salt systems, in the sense that the system is created by temperature-induced phase separation. More specifically, this means that a thermoseparating polymer is used, which polymer solution will separate into two phases when its temperature is increased to a point above its cloud point (CP). The above discussed PEG polymer can in fact be used as a thermoseparating polymer, but its high cloud point, which is 111.7° C. at a 10% solution in water, renders PEG systems highly unsuitable for separation of delicate biological materials. Thermoseparating two-phase systems have been suggested for partitioning of some proteins, such as enzymes, and for a water-soluble steroid.

More specifically, Harris et al. (P. A. Harris et al: Enzyme purification using temperature-induced phase formation, Bioseparation 2: 237-246, 1991) disclose the purification of the enzyme 3-phosphoglycerate kinase and hexokinase from a cell homogenate of baker's yeast in an aqueous two-phase system. The system used comprises a random copolymer of ethylene oxide (EO) and propylene oxide (PO) known as UCON 50-HB-5110 and dextran or hydroxypropyl starch. The EO-PO copolymer has a cloud point that is much lower than that of PEG, namely 50° C.

Further, Alred et al (Patricia A. Alred et al: Partitioning of ectdysteroids using temperature-induced phase separation, *Journal of Chromatography*, 628 (1993) 205-214) discloses a study of the partitioning of the ectdysteroids α-ecdysone and β-ecdysone in an aqueous two-phase system by thermoseparation. The system comprises the same components as the above-mentioned, namely the ethylene oxide-propylene oxide random copolymer UCON 50-HB-5100 and dextran. Due to the high levels of ecdysteroids recovered, 73.6% and 85.6%, respectively, such a system is suggested as an analytical or a preparative technique for ecdysteroids.

Finally, Persson et al (Persson et al: Purification of recombinant apolipoprotein A-1 expressed in *Escherichia coli* using aqueous two-phase extraction followed by temperature-induced phase separation, Journal of Chromatography B, 711 (1998) 97-109) describe a method of purification of recombinant apolipoprotein A1 in aqueous two-phase systems comprising ethylene oxide-propylene oxide random copolymers and hydroxypropyl starch. The polymer system is thermoseparating in the sense that it separates into one water-rich and one polymer-rich phase when heated above a critical point. It was shown that apolipoprotein could be partitioned to the top EO-PO copolymer phase while contaminating proteins and DNA was partitioned to the bottom phase.

In summary, there is still a need of improved methods for the purification of plasmid DNA from cell lysates.

SUMMARY OF THE PRESENT INVENTION

The object of the present invention is to provide a method for the purification of plasmid DNA, which avoids one or more of the above-discussed drawbacks of the prior art. This can be achieved by the method as defined in the appended claim 1.

Thus, one object of the invention is to provide a method, which is useful as a primary step in plasmid purification.

A specific object is to provide a method for the purification of plasmid DNA in an aqueous two-phase system, which results in a product wherein the salt concentration is lowered as compared to the prior art method.

Another object of the invention is to provide a method, which is capable of separating plasmid DNA from RNA and other impurities, such as protein and genomic DNA, in a cell lysate.

A further object of the invention is to provide a kit useful for separation of plasmid DNA from a cell lysate in an aqueous two-phase system comprising a thermoseparating polymer.

Other aspects and advantages of the present invention will appear from the detailed description of the present invention and the experimental part below.

DEFINITIONS

Figure 1:
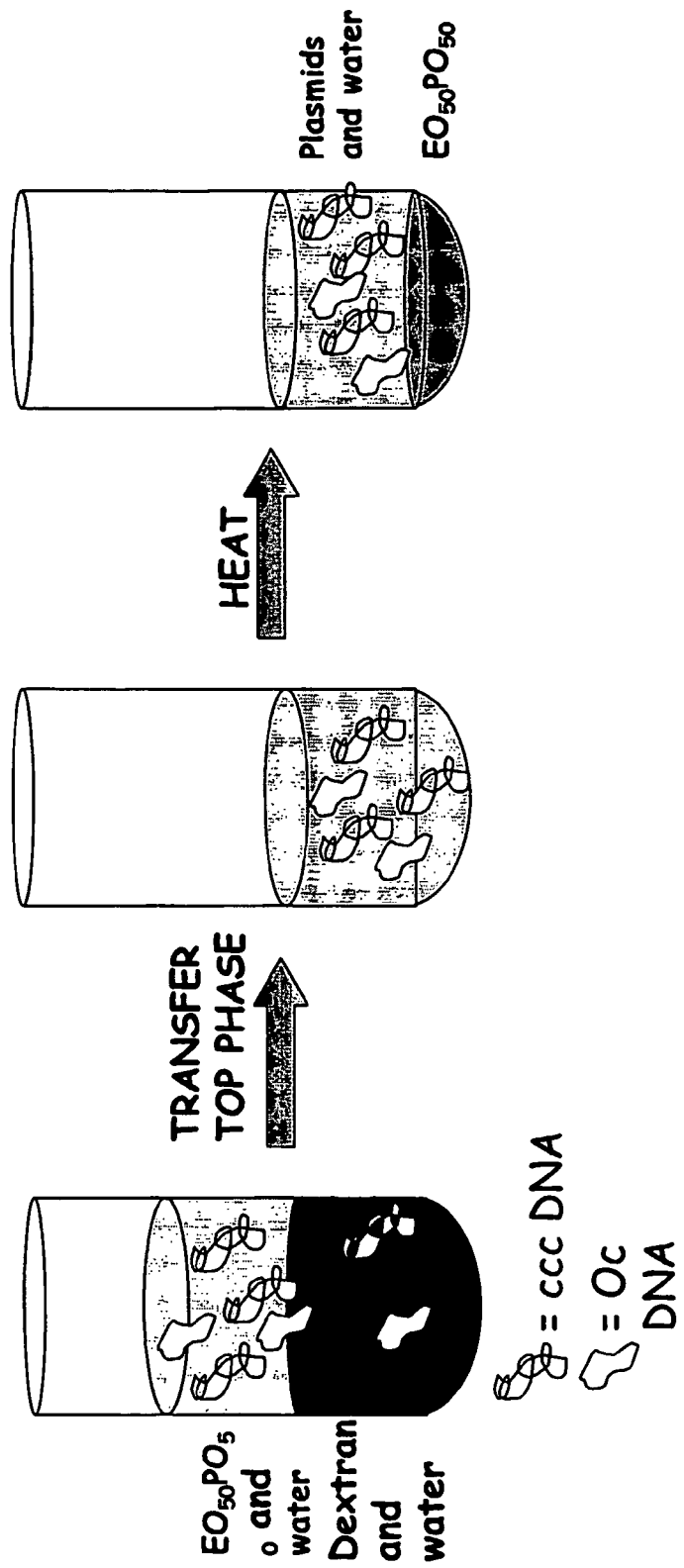
FIG. 1 is a schematic picture of the purification of plasmid DNA in a thermoseparating system comprising a first and a second polymer according to the invention. Plasmid DNA is partitioned to the top phase in the first system, the top-phase is then isolated and heated. A new two-phase system is obtained, wherein the plasmid DNA is recovered in the water phase.

The term "a biological solution" embraces any solution that comprises plasmid DNA, usually together with undesired contaminating components such as cell debris, proteins, RNA etc.

DETAILED DESCRIPTION OF THE INVENTION

A first aspect of the present invention is a method for the purification of plasmid DNA in an aqueous two-phase system, comprising the steps of
(a) providing a composition comprising a first polymer that exhibits inverse solubility characteristics, a second polymer that is immiscible in the first polymer and optionally a salt;
(b) contacting said solution with an aqueous solution comprising plasmid DNA;
(c) providing a phase separation and subsequently isolating the aqueous phase;
(d) increasing the temperature of the isolated phase to a temperature above the cloud point of the first polymer and below the temperature where plasmid DNA is degraded and subsequently isolating the aqueous phase so formed; and optionally
(e) a chromatography step to recover the plasmid DNA from the isolated top phase.

Thus, the first and the second polymers used in the present method are immiscible. More specifically, one polymer should be essentially hydrophilic and the other should be more hydrophobic but still water-soluble, i.e. amphiphilic. As the skilled person in this field will understand, the concentrations of the first and second polymer should be high enough to bring about a phase separation into at least two phases.

Thus, the first polymer is amphiphilic, water-soluble and capable to interact with plasmid DNA. That way, the plasmid DNA will be extracted into the more hydrophobic phase and thereby separated from more hydrophilic contaminants such as proteins, cells, cell debris etc. The term "inverse solubility" means that the solubility of the polymer varies inversely with the solution temperature, and more specifically, that the solubility of the polymer decreases with increasing solution temperature. Inverse solubility is therefore directly opposed to the temperature effect exhibited by most solutes. In the present context, the term "thermoseparating" is also used to denote the first polymer. Quite surprisingly, the present inventors have also shown that plasmid DNA can be separated from genomic DNA and RNA using the method according to the invention. In fact, the present invention shows for the first time that plasmid DNA can be obtained in a water solution free from polymer after extraction in an aqueous two-phase system.

Examples of suitable polymers useful as the first polymer that exhibits inverse solubility can e.g. be found in I.Y. Galaev et al., Enzyme Microb. Tech., vol 15 (1993), pp. 354-366. More specifically, in one embodiment, the first polymer is selected from the group that consists of polyalkylene glycols, such as hydrophobically modified polyalkylene glycols, poly (oxyalkylene)polymers, poly(oxyalkylene)copolymers, such as hydrophobically modified poly(oxyalkylene)copolymers, polyvinyl pyrrolidone, polyvinyl alcohol, polyvinyl caprolactam, polyvinyl methylether, alkoxylated surfactants, alkoxylated starches, alkoxylated cellulose, alkyl hydroxyalkyl cellulose, silicone-modified polyethers, and poly N-isopropylacrylamide and copolymers thereof. Derivatives and mixtures of the above-mentioned examples are also included within the scope of the present invention. Also, WO 98/11140

(Pharmacia & Upjohn AB) provides a more detailed description of suitable thermoseparating polymers useful in the present method. In an advantageous embodiment of the present method, the first polymer is a copolymer comprised of ethylene oxide and propylene oxide. In a preferred embodiment, the copolymer is comprised of about 50% of ethylene oxide and about 50% of propylene oxide. Polymers of this kind are commercially available, such as Breox PAG 50 A 1000 (available from Laporte Performance Polymers, Southampton, U.K).

The concentration of the first polymer in the aqueous solution can be in the range of from about 0.5% up to about 30% by weight of the total weight of the aqueous solution, preferably within the range of about 3-20% by weight, more preferably within the range of about 4-15% by weight and most preferably about 4.5% by weight.

The second polymer is as mentioned above less hydrophobic than the first polymer and water-soluble. The molecular weight of the second, hydrophilic polymer may be in the range of from about 3,000-5,000,000, such as 10,000-5000,000 and preferably in the range from 40,000-500,000. In an advantageous embodiment of the present method, the second polymer is selected from the group that consists of hydroxyalkyl cellulose, hydroxyalkyl starches, starch, dextran, pullulan and derivatives and mixtures thereof. Polymers of this kind are also commercially available, such as e.g. Dextran 500 T (Amersham Biosciences AB, Uppsala, Sweden). The concentration of the second polymer in the aqueous solution can be in the range of from about 1% up to about 30% by weight of the total weight of the aqueous solution, preferably within the range of about 3-20% by weight, more preferably within the range of about 4-15% by weight and most preferably about 4.5% by weight.

The present invention also encompasses the use of three or more polymers. Such multiphase separation can be designed by the skilled person in this field by selecting suitable combinations of three or more polymers and sufficiently high concentrations thereof when contacted with the aqueous solution.

As the skilled person in this field will realise, the concentration of plasmid DNA in the aqueous solution, i.e. the primary system, will depend on its origin. For example, if the aqueous solution is a cell lysate, the concentration of plasmid DNA in the starting material will depend on the production host. The concentration of plasmid DNA in the primary system is typically between 0.1 μg/ml-500 μg/ml.

As appears from the above, in one embodiment of the method according to the invention, the weight ratio of the amounts of first polymer:second polymer is about 1:1. In an advantageous embodiment of the present method, the amount of the first polymer is 4.5% (w/w) and the amount of the second polymer is 4.5% (w/w) of the composition provided in step (a). This embodiment is especially advantageous if a more extreme partitioning to the top phase is desired.

The partitioning of plasmid DNA to the hydrophobic phase can be enhanced by adding a compound with a hydrophobic cation or, alternatively, a hydrophilic anion, to the aqueous solution. Suitable compounds include inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions such as phosphates, sulphate, nitrate, chloride and hydrogen carbonate. Specific examples are triethyl ammonium sulphate and sodium phosphate. The concentration of a compound with a hydrophobic cation or hydrophilic anion should be selected to give an enhanced partitioning effect, while at the same time avoiding precipitation of plasmid DNA.

The partitioning of molecules between the phases of two-phase systems is described by the partitioning coefficient K, which is defined as $$K = C_T/C_B \qquad (1)$$

wherein
$C_T$=the concentration in the top phase of the molecule of interest $C_B$=the concentration in the bottom phase of the molecule of interest.

The partitioning of molecules between the phases of the two-phase systems can be shown in phase diagrams, wherein the borderline between one and two phases is called the binodial curve. The polymer concentration of the two phases in equilibrium with each other are described by tie lines in the phase diagram. Increase of the polymer concentration, i.e. increase of the tie line length, leads, to more extreme partitioning in two-phase systems (see G. Johansson, Methods in Enzymology, vol. 228 (1994) pp. 28-42). The skilled person in this field can easily perform experiments for arriving at conditions for suitable partitioning between the two phases.

In one embodiment of the present method, the aqueous solution that comprises plasmid DNA is a cell lysate, which method comprises a step for desalting the cell lysate before step (b).

After the contact of step (b), the plasmid DNA is partitioned to the hydrophobic phase. As mentioned above, this partitioning can be enhanced by adding a compound such as a salt. As is well known, addition of salt will also decrease the cloud temperature of the first polymer, and accordingly the phase separation provided in step (d) could use a lower temperature in that case. In the most convenient embodiment of the present method, the mixing according to step (b) and the partitioning according to step (c) are performed at room temperature. This first phase separation results in a top phase comprising the first polymer and plasmid DNA in water, while the lower phase contaminating RNA and proteins in the second polymer and water.

In step (c), the top phase comprising the plasmid DNA is isolated in a separate container. In this second phase separation of the present method, the isolated phase is heated to a temperature above the cloud point of the thermoseparating polymer, which as mentioned above will depend on the salt concentration in the sample. However, in a preferred embodiment, the temperature is increased, preferably in a water bath, to a temperature above about 40° C., such as about 50° C. The heating results in a phase separation, wherein the top phase comprises the plasmid DNA and the lower phase comprises the polymer. Thus, the plasmid DNA is obtained in a water phase which is essentially free of polymer, since the polymer content in the top phase has been shown to comprise less than 1% polymer. In addition, the salt concentration in the solution wherein the plasmid DNA is obtained can be much lower than in the suggested prior art method wherein plasmid DNA is salted out.

Accordingly, the product obtained from the method according to the invention will be more advantageous than the prior art products for applications wherein a high degree of purity is a requirement, such as for gene therapy. Compared to other methods, such as a series of chromatographic steps, aqueous two-phase systems are known to be easy to scale up, since the partitioning is essentially independent of the size of the system.

A last embodiment of this first aspect is a method for purification of plasmid DNA from a lysate, which comprises a first step of desalting the lysate, a second step for recovery which comprises the method described above, and a last step of chromatography for final purification of the plasmid DNA. The desalting can be performed by any suitable method. In one embodiment, the desalting is performed by a method selected from the group that consists of gel filtration, diafiltration and ultrafiltration.

A second aspect of the present invention is a composition for extraction of plasmid DNA in an aqueous two-phase system, which composition comprises a first polymer that exhibits inverse solubility characteristics at temperatures below about 60° C., a second polymer that is immiscible in the first polymer and optionally a salt. The first and the second polymers are as discussed above in relation to the method according to the invention.

In one embodiment of the present composition, the amount of the first polymer is 4.5% (w/w) and the amount of the second polymer is 4.5% (w/w).

In a preferred embodiment, the present composition is for separation using a method according to the invention.

A third aspect of the present invention is a kit for purification of plasmid DNA from a cell lysate in an aqueous two-phase system, which kit comprises a first polymer that exhibits inverse solubility characteristics at temperatures below about 60° C., a second polymer that is immiscible in the first polymer and optionally a salt in one compartment as well as written instructions for the use thereof.

The first polymer is as discussed above. In an advantageous embodiment of the present kit, the first polymer is comprised of ethylene oxide and propylene oxide. In an advantageous embodiment, said copolymer is comprised of about 50% of ethylene oxide and about 50% of propylene oxide. Such copolymers are as discussed in detail above.

In an advantageous embodiment of the present kit, the second polymer is selected from the group that consists of hydroxyalkyl cellulose, hydroxyalkyl starches, starch, dextran, pullulan and derivatives and mixtures thereof, as discussed in more detail above in relation to the method according to the invention.

In a specific embodiment of the present kit, the weight ratio of the amounts of first polymer:second polymer is about 1:1.

In a preferred embodiment of the kit, the amount of first polymer is 4.5% (w/w) and the amount of second polymer is 4.5% (w/w).

In the preferred embodiment, the present kit is for purification of a cell lysate that has been desalted before being mixed with an aqueous solution that comprises plasmid DNA.

In an advantageous embodiment the present kit is for use in a method according to the present invention.

A fourth aspect of the present invention is the use of a polymer that exhibits inverse solubility characteristics at temperatures below about 60° C. in an aqueous two-phase system for the purification of plasmid DNA from a cell lysate.

The first polymer is as discussed above. In an advantageous embodiment, the polymer is a copolymer of ethylene oxide and propylene oxide. In the preferred embodiment, the copolymer is comprised of about 50% of ethylene oxide and about 50% of propylene oxide.

In order to provide a two-phase system, the polymer is used together with a second polymer that is immiscible therein. In the preferred embodiment, the second polymer is selected from the group that consists of hydroxyalkyl cellulose, hydroxyalkyl starches, starch, dextran, pullulan and derivatives and mixtures thereof. In the most preferred embodiment, the second polymer is dextran. However, the second polymer can be as discussed above in relation to the method according to the invention.

Finally, the present invention also encompasses the use of a polymer selected from the group that consists of hydroxyalkyl cellulose, hydroxyalkyl starches, starch, dextran, pullulan and derivatives and mixtures thereof in an aqueous two-phase system for the purification of plasmid DNA from a cell lysate, wherein the purification is obtained by temperature-induced phase separation.

DETAILED DESCRIPTION OF THE DRAWINGS

FIG. 1 is a schematic picture of the purification of plasmid DNA in system according to the invention, wherein the thermoseparating polymer is $EO_{50}PO_{50}$ and the second polymer is Dextran T 500 (Amersham Biosciences AB, Uppsala, Sweden). The different forms of plasmid DNA are partitioned to the top phase in the first system. The top phase is then isolated in a new container and heated to a temperature above its cloud point (CP). A new two-phase system is obtained where the plasmid DNA is recovered in the water phase free from polymer.

Figure 2:
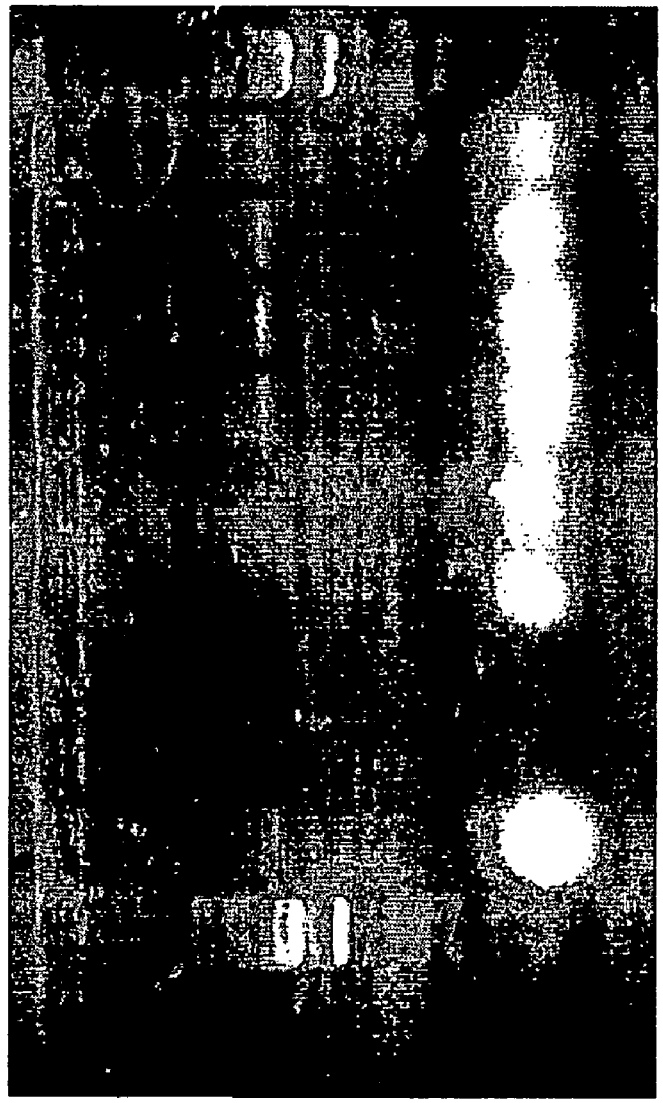
FIG. 2 shows an agarose gel analysis of top and bottom phases from a thermoseparating system comprising a first and a second polymer and 50 mM $Na_2HPO_4$ buffer system according to the invention.

FIG. 2 shows an agarose gel analysis of top and bottom phases from a thermoseparating $EO_{50}PO_{50}$/Dextran T 500 and 50 mM $Na_2HPO_4$ according to the invention. A volume of 12 µl sample was added to each lane. The agarose gel was stained with ethidium bromide. More specifically, lane 1 is a blank;

lane 2 is a molecular weight marker; lane 3 is a desalted alkaline lysate; lane 4 is the bottom phase from thermoseparated system; lane 5 is the bottom phase from thermoseparated system; lane 6 is the bottom phase primary system; lane 7 is the bottom phase primary system; lane 8 is a thermoseparated top phase; lane 9 is a thermoseparated top phase; lane 10 is the top phase primary system; lane 11 is the top phase primary system; and lane 12 is a molecular weight marker. Here, the term "primary system" refers to the first phase separation provided according to step (c) of the present method, while the term "thermoseparated system" refers to the phase separation provided according to step (d) of the present method.

Figure 3:
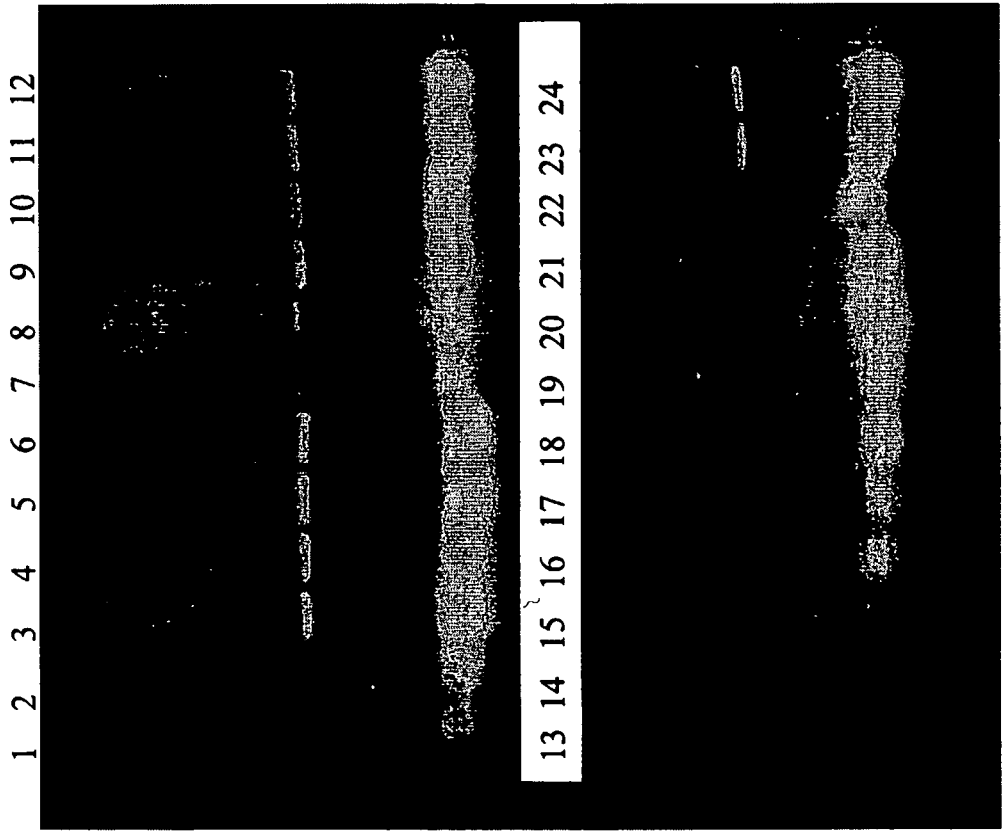
FIG. 3 shows an agarose gel analysis of top and bottom phases from a thermoseparating system comprising a first and a second polymer and 50 mM $Na_2HPO_4$ buffer system according to the invention, wherein the dilution of the thermoseparated top phase has been varied.

FIG. 3 shows an agarose gel analysis of top and bottom phases from a thermoseparating $EO_{50}PO_{50}$/Dextran T 500 and 50 mM $Na_2HPO_4$ according to the invention. The agarose gel is stained with SYBR green. A volume of 12 µl was added to each lane. More specifically, lane 1 is a thermoseparated top phase 5× diluted; lane 2 is a thermoseparated top phase 5× diluted; lane 3 is a thermoseparated top phase 2× diluted; lane 4 is a thermoseparated top phase 2× diluted; lane 5 is a thermoseparated top phase 1× diluted; lane 6 is a thermoseparated top phase 1× diluted; lane 7 is a top phase primary system 5× diluted; lane 8 is a top phase primary system 5× diluted; lane 9 is a top phase primary system 2× diluted; lane 10 is a top phase primary system 2× diluted; lane 11 is a top phase primary system 1× diluted; lane 12 is a top phase primary system 1× diluted; lane 13 is a bottom phase from thermoseparation 5× diluted; lane 14 is a bottom phase from thermoseparation 2× diluted; lane 15 is a bottom phase from thermoseparation 1× diluted; lane 16 is a bottom phase primary system 5× diluted; lane 17 is a bottom phase primary system 5× diluted; lane 18 is a bottom phase primary system 2× diluted; lane 19 is a bottom phase primary system 2× diluted; lane 20 is a bottom phase primary system 1× diluted; lane 21 is a bottom phase primary system 1× diluted; lane 22 is a desalted alkaline lysate 5× diluted; lane 23 is a desalted alkaline lysate 2× diluted; and lane 24 is a desalted alkaline lysate 1× diluted.

Figure 4:
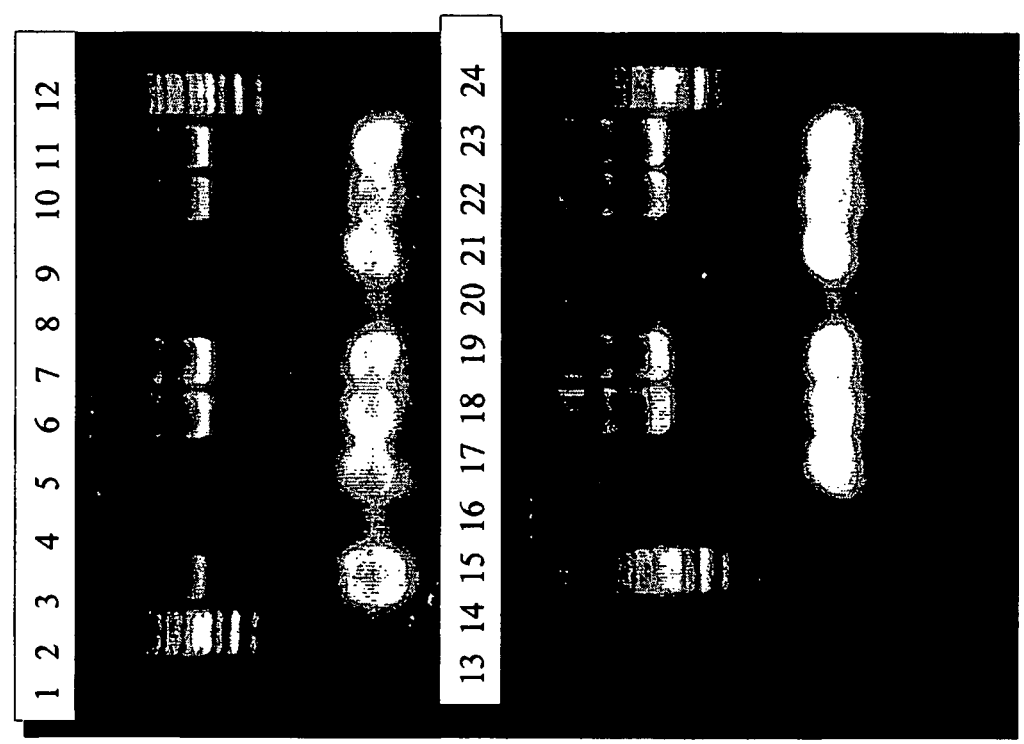
FIG. 4 shows an agarose gel analysis of thermoseparating system comprising a first and a second polymer and 50 mM $Na_2HPO_4$ buffer system according to the invention, wherein the first polymer/second polymer concentration has been varied in the primary system.

FIG. 4 shows an agarose gel analysis of thermoseparating $EO_{50}PO_{50}$/Dextran T 500 and 50 mM $Na_2HPO_4$ according to the invention. The systems are composed of different polymer concentrations:

4/6=4% (w/w) $E_{50}PO_{50}$/6% (w/w) Dextran T 500,

3/7=3% (w/w) $E_{50}PO_{50}$/7% (w/w) Dextran T 500,

3/8=3% (w/w) $EO_{50}PO_{50}$/8% (w/w) Dextran T 500, 2.5/9=2.5% (w/w) $EO_{50}PO_{50}$/9% (w/w) Dextran T 500.

All systems contain 50 mM 50 mM $Na_2HPO_4$. A volume of 12 μl sample is added to each lane. The agarose gel is stained with ethidium bromide.

More specifically, in FIG. 4, lane 1 is a blank; lane 2 is a molecular weight marker; lane 3 is a desalted alkaline lysate; lane 4 is the bottom phase from thermoseparation in a 3/7 system; lane 5 is the bottom phase from the primary step in a 3/7 system; lane 6 is the thermoseparated top phase in a 3/7 system; lane 7 is the top phase from the primary system in a 3/7 system; lane 8 is the bottom phase from the thermoseparation in a 4/6 system; lane 9 is the bottom phase from the primary system in a 4/6 system; lane 10 is the thermoseparated top phase in a 4/6 system; lane 11 is the top phase from the primary system in a 4/6 system; lane 12 is a molecular weight marker; lane 13 is a blank; lane 14 is a blank; lane 15 is a molecular weight marker; lane 16 is the bottom phase from thermoseparation in a 2.5/9 system; lane 17 is the bottom phase from a primary system in a 2.5/9 system; lane 18 is the thermoseparated top phase in a 2.5/9 system; lane 19 is the top phase from a primary system in a 2.5/9 system; lane 20 is the bottom phase from the thermoseparation in a 3/8 system; lane 21 is the bottom phase from a primary system in a 3/8 system; lane 22 is the thermoseparated top phase in a 3/8 system; lane 23 is the top phase from a primary system in a 3/8 system; and lane 24 is a molecular weight marker.

Figure 5:
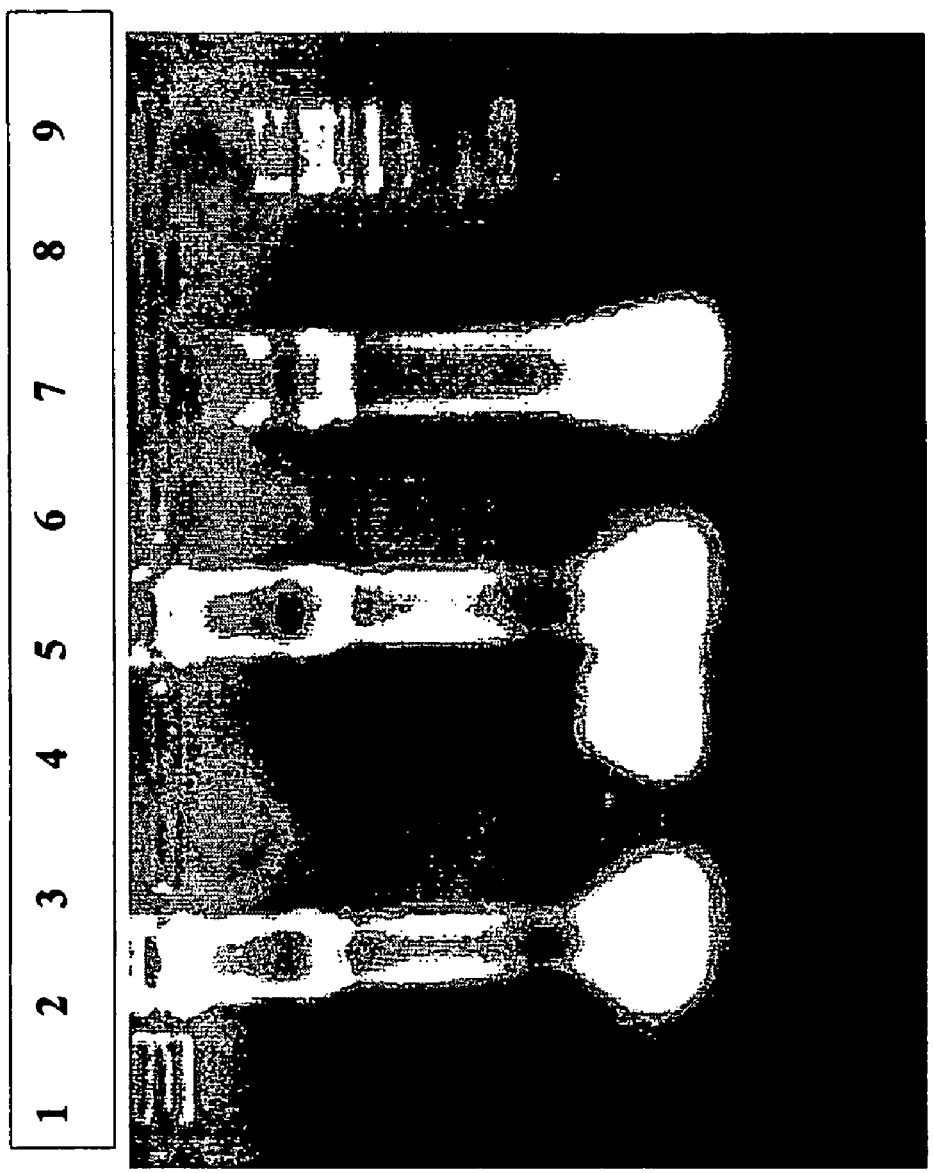
FIG. 5 shows agarose gel electrophoresis (0.8% w/v) of top and bottom phases from extraction of a diafiltrated lysate in an aqueous two-phase system as described in example 2 below.

FIG. 5 shows agarose gel electrophoresis (0.8% w/v) of top and bottom phases from extraction of a diafiltrated lysate in an aqueous two-phase system as described in example 2 below. More specifically, in FIG. 5, lane 1 is the thermoseparated bottom phase; lane 2 is the thermoseparated top-phase; lane 4 is the bottom phase (primary system); lane 5 is the top phase (primary system); lane 7 is the diafiltrated lysate (starting material); and lane 9 is the Mw marker.

Figure 6:
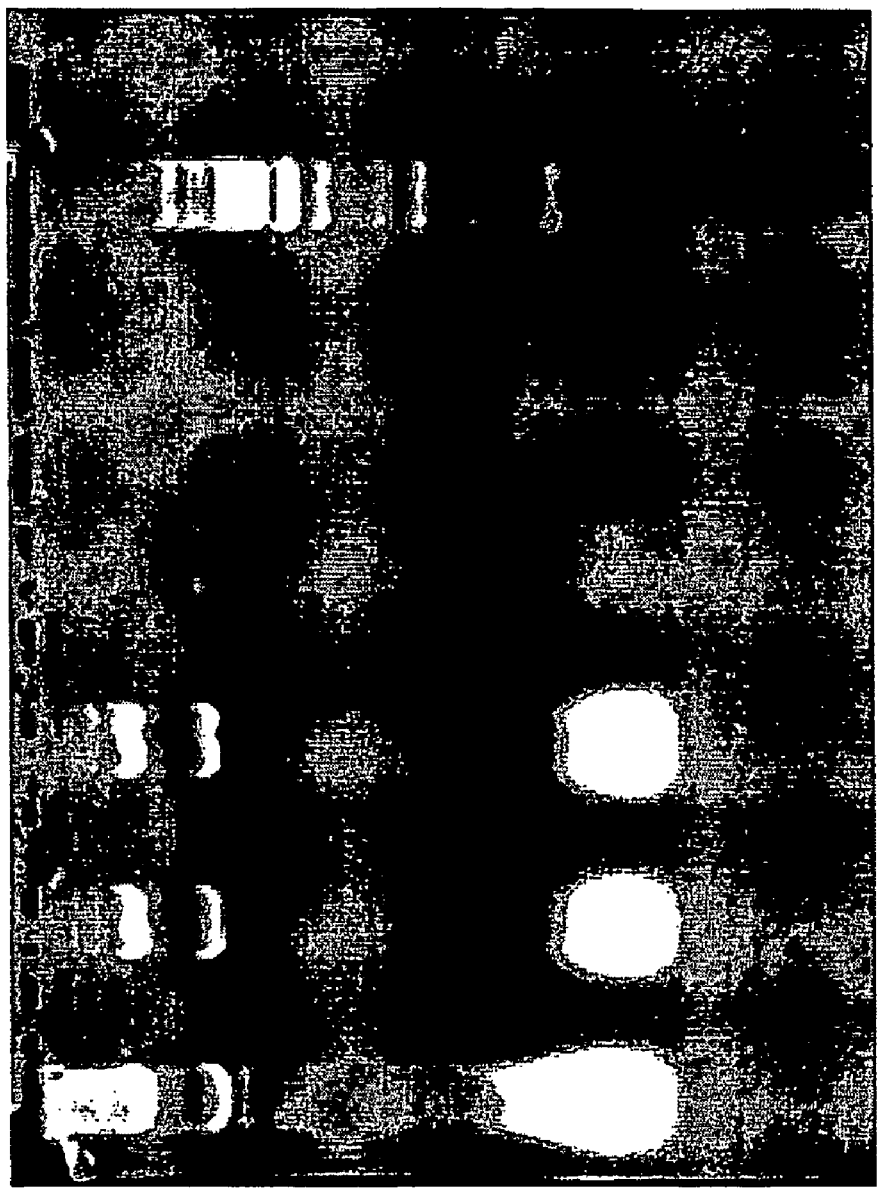
FIG. 6 shows agarose gel electrophoresis (0.8% w/v) of top and bottom phases from extraction of an ultrafiltrated lysate in an aqueous two-phase system as described in example 3 below.

FIG. 6 shows agarose gel electrophoresis (0.8% w/v) of top and bottom phases from extraction of an ultrafiltrated lysate in an aqueous two-phase system as described in example 3 below. More specifically, in FIG. 6, lane 1 is the ultrafiltrated lysate (starting material); lane 2 is the top phase in primary system; lane 3 is the thermoseparated top phase; lane 4 is the thermoseparated bottom phase; and lane 5 is the Mw marker.

EXPERIMENTAL PART

The following examples are provided for illustrative purposes only and are not to be construed as limiting the scope of the present invention as defined by the appended claims. All references given below and elsewhere in the present application are hereby included by reference.

Material and Methods

Chemicals

The polymer Breox PAG 50 A 1000 (EO50PO50) (Mr 3900) was obtained from Laporte Performance Chemicals (Southampton, U.K.) and Dextran T 500, with a molecular weight of 500,000, is available from Amersham Biosciences AB (Uppsala, Sweden). $Na_2HPO_4$ was obtained from Merck Eurolab. A high copy number plasmid pUC 19 (2.686 kb) with a JV4 insert (3.433 kb) was a gift from Amersham Biosciences. The plasmid is referred to as pJV4 later on in the text (Vasi 1999).

Cultivation

The plasmid pJV4 was cultivated in *E. coli* strain TG1α over night in 2.0 L baffled shake flasks using 500 ml Lauria broth (10 g/L NaCl, 10 g/L Tryptone and 5 g/L Yeast extract). The ampicillin concentration in the cultivations was 100 μg/ml and grown overnight at 37° C. at 250 rpm.

Alkaline Lysis

A modified alkaline lysis method was used. A 500 ml overnight cell culture was harvested by centrifugation at 9000 rpm in a Sorvall SLA 3000-rotor for 10 min at 4° C. The supernatant is carefully removed and 5 g of the bacterial pellet was resuspended by vortexing in 36 mL suspension buffer consisting of 61 mm glucose, 10 mM Tris, 50 mM EDTA (pH 8). After the cells are completely resuspended, 78 mL of lysis buffer P2 (0.2 M NaOH, 1% SDS) was added while stirring gently with a magnetic stirrer. The mixture was incubated for 10 min at room temperature while stirring, assuring a complete mixture (1 phase) is achieved. A volume of 58.6 mL of ice cold neutralisation buffer (5 M potassium acetate, pH 5.5) was added to the lysate. The solution was kept in an ice-bath on a magnetic stirrer for at least 20 min. A white precipitate was formed containing genomic DNA, proteins and cell debris. The precipitate was then removed by centrifugation in an SS-34-rotor at 4° C. for 30 minutes at 10 000 rpm. The supernatant is then carefully removed to a fresh tube and stored in the refrigerator.

Example 1

Separation of Plasmid pJV4 from an *E. coli* Lysate, Desalting by Gel Filtration The alkaline lysate was desalted by gel filtration on a Sephadex™ G-25 (Amersham Biosciences AB, Uppsala, Sweden) matrix. More specifically, the Sephadex beads were packed in a XK 50/30 column (Amersham Biosciences AB, Uppsala, Sweden), giving a total bed volume of 225 ml. The column was integrated to an ÄKTA™ explorer 10 system (Amersham Biosciences AB, Uppsala, Sweden) and equilibrated with the mobile phase (5 mM sodium phosphate buffer). Samples to be desalted (50-100 ml) were pumped into the column by the sample pump P-950 at a flow rate of 5 ml/min. The eluate from the column was monitored by UV absorbance and conductivity, which ensured an appropriate fractionation of nucleic acid containing eluate in 5 mM sodium phosphate buffer.

Aqueous Two-Phase Systems

Systems of a total weight of 10 g, containing 4.5% (w/w) Dextran T 500 and 4.5% (w/w) $EO_{50}PO_{50}$ were made up by weighing appropriate amounts of a 25% stock solution of dextran and 100% $EO_{50}PO_{50}$ stock solution in 10 mL graduated test tubes. The buffer salts used were 50 mM $Na_2HPO_4$ and was added to the system from a 1 M stock solution. The clarified and desalted alkaline lysate was added to a final weight of 10 g. The systems were mixed carefully until all polymers were dissolved and the phases were then separated by centrifugation (1600 g, 10 minutes) at room temperature. The volume of the top and bottom phase was determined. The phases were separated and isolated in new containers. The top phase was placed in a water bath at 55° C. for three minutes and then centrifuged for two minutes to obtain one water phase and one concentrated polymer phase.

Agarose Gel Electrophoresis

The top and bottom phases from the phase system were analysed on an agarose gel. The agarose gel was run in a Hoefer™ HE 33 mini submarine electrophoresis unit from Amersham Biosciences AB. A 0.8% (w/v) agarose (Duchefa, Netherlands) gel containing 15 µg/ml ethidium bromide (Quantum Biotechnologies, USA) was run for 90 V and 30 min. The gel was analysed and photographed under UV light.

Results Example 1

Polymer Concentration and Salt Effects

The partitioning of desalted alkaline lysate containing the plasmid DNA in an aqueous two-phase system can be influenced by different factors such as polymer concentration and salt composition. The object was to obtain a one sided partitioning of the plasmid to the $EO_{50}PO_{50}$ phase in the primary aqueous two-phase system (FIG. 1.). By altering the concentration of the polymers in a two-phase system, plasmid DNA can be more extremely partitioned to the top phase. Partitioning of plasmid DNA in desalted alkaline lysate in two-phase systems composed of different concentrations of $EO_{50}PO_{50}$ and Dextran T 500 was studied. By decreasing the polymer concentration in both phases a more extreme partitioning to the top phase was achieved (FIG. 2.). Qualitative analysis on an agarose gel electrophoresis shows that by decreasing the polymer concentration from 7% (w/w) Dextran T 500/7% (w/w) $EO_{50}PO_{50}$ to 4.5% (w/w) Dextran T 500 and 4.5% (w/w) $EO_{50}PO_{50}$, plasmid DNA can be partitioned to the top phase. It has earlier been described in the literature (Albertson, 1986) that DNA can effectively be transferred between phases by addition of a suitable salt. To achieve a dominating effect of the salt in a two-phase system, the concentration of the salt must be at least ten times higher then the buffer. The addition of a salt to a two-phase system forces the anion and the cation to partition together between the two different polymer phases and this will generate an electrical potential between the phases. The $HPO_4^{2-}$ anion has affinity for the dextran phase. This will create an electrochemical driving force in the system. If a negatively charged substance e.g. plasmid DNA is added to this system, the DNA will partition to the top phase (FIG. 2).

Partitioning of Plasmid DNA in a Thermoseparating System

The lysate was partitioned in systems containing 4.5% (w/w) Dextran T 500, 4.5% (w/w) $EO_{50}PO_{50}$ and 50 mM $Na_2HPO_4$. The systems were prepared according to the section "Material and methods" above. The systems were mixed and after phase separation the phases were separated and isolated in separate containers. The top phase was put in a water bath at 55° C. The system phase separated into two new phases, one water phase and one dense polymer phase. The thermoseparating step was utilised for separating the target plasmid from the $EO_{50}PO_{50}$ polymer, and isolating the plasmid in a water phase with low (<1%) polymer solution. The phases were analysed on an agarose gel electrophoresis stained with ethidium bromide (FIG. 2.) From the agarose gel electrophoresis it can be seen that all forms of plasmid DNA are partitioned to the top phase in the first step and in the thermoseparating step the plasmid DNA is exclusively partitioned to the top water phase. From the agarose gel electrophoresis (FIG. 2.) it can also be seen that contaminating RNA is to a high degree partitioned to the bottom phase in the primary system. By staining the agarose gel with SYBR green (Molecular Probes) a 25 times higher sensitivity in detection of DNA can be achieved compared to staining of DNA with ethidium bromide (FIG. 2). The use of a more sensitive staining method conclusively indicates that the plasmid DNA could be partitioned to the top phase in the primary system and the water phase in thermoseparating system. No plasmid DNA is partitioned to the bottom phase neither in the primary step nor in the thermoseparating step.

Partitioning of Total Protein

In the primary purification step in a process for plasmid isolation the main objective is to remove the dominating contaminants in the solution containing the plasmid DNA. When the bacteria are lysed in the alkaline lysis step protein, RNA, genomic DNA, cells and cell debris are released. After the neutralisation step in the alkaline lysis the lysate is centrifuged and most of these contaminants are removed but there will still be significant contaminants present in the sample. Analysis of the total protein partitioning in the first step showed a K value of 1.4. This gives a 65% yield of total protein in the top phase. The system can discard 35% of the proteins in the first step. In the thermoseparation step the yield of the protein is 100%. Thus, the system can discard proteins to an extent of 35%.

Concentration of the Plasmid DNA

When a primary purification step is designed one of the issues are to decrease the process volume of the working solution. In a two-phase system this can be achieved by decreasing the volume of the top-phase. By moving along a tie-line in a phase diagram the volume ratio between the two phases can be altered without changing the partitioning of the substance. If the dextran concentration is increased in the bottom phase a larger volume of the bottom phase is created and thus decreasing the volume of the top phase. Four different systems composed of 4.5% (w/w) $EO_5PO_5$/4.5% (w/w) Dextran T 500, 4% (w/w) $EO_{50}PO_{50}$/6% (w/w) Dextran T 500, 3% (w/w) $EO_{50}PO_{50}$/7% (w/w) Dextran T 500, 3% (w/w) $EO_{50}PO_{50}$/8% (w/w) Dextran T 500 and 2.5% (w/w) $EO_{50}PO_{50}$/9% (w/w) Dextran T 500 were studied. Analysis of the systems on agarose gel (FIG. 4.) shows that the extreme partitioning of plasmid DNA can still be achieved if the volume is decreased in the top-phase. In the system comprising of 2.5% (w/w) $EO_{50}PO_{50}$/9% (w/w) Dextran T 500 a volume ratio ($V_T/V_B$) between the top and bottom phase was 0.24. This leads to a concentration in the top phase of the isolated plasmid by a factor of 3 relative the alkaline lysis solution. In all of these systems RNA is partly discarded to the bottom phase.

Analysis of Plasmid DNA on Group Separation Chromatography

Analysis of plasmid DNA was performed on group separation chromatography. Separation between all forms of plasmid DNA and RNA can be achieved. Results show that the total yield of the plasmid in the top water phase after thermoseparation compared to the starting material is 103.3%. The yield of RNA in the same sample according to chromatography results is 27%. This means that the aqueous two-phase system is able to remove 63% of the contaminating RNA.

Example 2

Separation of Plasmid pJV4 from an *E. coli* Lysate, Desalting by Diafiltration A total amount of 75 g cell paste from TG1/pJV4 cells were lysed and further treated as described in Example 1 above. The final lysate volume was 2 L after final preparations.

Diafiltration

A polysulfon hollow fibre cartridge (A/G Technology Corporation, Needham, Mass., USA) with a 100 000 Da cut off was used for diafiltration (Lot no. 96992057061, Lumen id: 0.5 mm, area 650 m$^2$). Before use, the cartridge was washed with MilliQ water to remove contaminants of glycerol. The system was recirculated with 5 l of MilliQ water for 10 min and than with fresh 5 mM of Na-phosphate buffer for 10 min. A volume of 350 ml clarified lysate was diafiltrated towards a 5 mM Na-phosphate buffer pH 7.0. For complete buffer exchange, four sample volumes of 5 mM Na-phosphate buffer was used. Final retentate volume after diafiltration was 300 ml, which gave a volume reduction from 350 ml to 300 ml. After diafiltration the column was washed with 100 ml 5 mM buffer to remove bound plasmid DNA from the column.

A second diafiltration was performed since four buffer volumes of buffer were not enough for complete buffer exchange. The diafiltrated lysate was diafiltrated once more towards a 5 mM NaP buffer, pH 7. Another 8 buffer volumes were used to achieve complete buffer exchange. The final diafiltrated sample was further extracted in an aqueous two-phase system.

Aqueous Two-Phase Systems

The systems were prepared as described in Example 1 above.

Results Example 2

Partitioning of Diafiltrated Plasmid DNA in a Thermoseparating System

The diafiltrated lysate was partitioned in an aqueous two-phase system composed of 4.5% (w/w) EO$_{50}$PO$_{50}$, 4.5% (w/w) Dextran T 500 and 50 mM Na$_2$HPO$_4$. All chemicals and the diafiltrated lysate was added to a glass tube to a final weigtht of 10 g. The system was then separated by centrifugation (1600 g, 10 min) at room temperature. The phases were separated in one top phase and one bottom phase and isolated in new containers.

The top phase was put in a water bath at 55° C. The system phase separated into two new phases, one water phase and one dense polymer phase. The thermoseparating step was utilised for separating the target plasmid from the EO$_{50}$PO$_{50}$ polymer, and isolating the plasmid in a water phase with low (<1%) polymer solution (FIG. 1). The phases from the aqueous two-phase extraction were analysed with agarose gel electrophoresis and size exclusion chromatography (group separation). The results from the group separation showed a one sided partitioning of the plasmid to the top phase (Table 1). The calculations of the concentration of the plasmid DNA are performed from a standard curve. From the agarose gel electrophoresis (FIG. 5.) it can be seen in lane 4 that no plasmid is partitioned to the bottom phase in the first extraction step while a lot of the RNA is discarded. Thus, a desalting of the alkaline lysate with diafiltration can be achieved followed by extraction in an aqueous two-phase system. A yield of 100% in the thermoseparated top phase can be achieved.

TABLE 1

Results from the group separation chromatography on a diafiltrated lysate and the phases from the extraction from an aqueous two-phase system.

| Sample | A 260 mAu | Dilution | Conc (µg/ml) | Amount pDNA (mg) | Vol. (ml) | Rec. (%) |
|---|---|---|---|---|---|---|
| Diafiltrated lysate (Start material in ATPS) | 1163.9 | 2 | 160.6 | 1.152 | 7.175 | 100 |
| Thermoseparated top phase 1 | 1743.5 | 2 | 240.6 | 1.126 | 4.68 | 97.8* |
| Thermoseparated top phase 2 | 1835.6 | 2 | 253.3 | 1.185 | 4.68 | 103* |

\# Conc factor is calculated as V starting lysate (ml)/V Diafiltrated lysate (ml)
*Recovery calculated as amount pDNA in thermoseparated top phase/ amount pDNA in lysate. Double samples.

Example 3

Separation of Plasmid pJV4 from an *E. coli* Lysate, Desalting by Ultrafiltration A total amount of 75 g cell paste from TG1/pJV4 cells were lysed and further treated as described in Example 1 above. The final lysate volume was 2 L after final preparations.

Ultrafiltration

The same cartridge with same cut off as earlier described for diafiltration was also used for ultrafiltration. A volume of 1000 ml of clarified lysate was ultrafiltrated until a volume of 225 ml was reached. The ultrafiltrated lysate was than dialysed against 800 ml of 5 mM NaP buffer. The lysate was dialysed until the buffer was finished. The lysate was than ultrafiltrated again until a final volume of 72 ml and further extracted in an aqueous two-phase system.

Results Example 3

Partitioning of Ultrafiltrated Plasmid DNA in a Thermoseparating System

The ultrafiltrated lysate was partitioned in an aqueous two-phase system as described earlier. From the agarose gel electrophoresis (FIG. 6.) it can be seen that an almost one sided partition was achieved of the plasmid. A small loss of the plasmid to the bottom phase is achieved in this system. This is probably due to the high plasmid concentration in the system e.g. 2 mg/ml or another possibility could be insufficient buffer exchange. The results of samples from ultrafiltration and two-phase extraction are presented in table 2. The ultrafiltrated lysate is concentrated 13.9 times from the starting material. No precipitation of RNA and DNA was visible in the ultrafiltrated lysate. Both a buffer exchange and a concentration of the lysate can be achieved with ultrafiltration. The ultrafiltrated lysate was compatible with the aqueous two-phase system but with some loss of the plasmid DNA to the bottom phase depending either on capacity limitations of the aqueous two-phase system or incomplete buffer exchange. The yield of plasmid DNA in the thermoseparated top phase was 85%.

TABLE 2

Results from group separation chromatography for an ultrafiltrated lysate and a thermoseparated top-phase from two-phase extraction.

| Sample | A 260 mAu | Dilution | Conc (μg/ml) | Amount pDNA (mg) | Vol. (ml) | Rec. (%) |
|---|---|---|---|---|---|---|
| Ultrafiltrated lysate (Start material in ATPS) | 514.117 | 50 | 1773.7 | 12.73 | 7.175 | 100 |
| Thermo-separated top phase | 692.7 | 50 | 2389.8 | 10.75 | 4.5* | 85* |

\# Conc factor is calculated as V starting lysate (ml)/V Diafiltrated lysate (ml)
*Recovery calculated as amount pDNA in thermoseparated top phase/amount pDNA in lysate

What is claimed is:

1. A method for the purification of plasmid DNA in an aqueous two-phase system, comprising:
   (a) providing a composition including a first polymer $EO_{50}PO_{50}$, a second polymer Dextran T 500 and, optionally, a salt;
   (b) contacting said composition with an aqueous solution comprising plasmid DNA and RNA to form a mixture which contains from about 4.5% (w/w) $EO_{50}PO_{50}$/4.5% (w/w) Dextran T 500, to about 2.5%(w/w)$EO_{50}PO_{50}$/9% (w/w) Dextran T 500;
   (c) providing a phase separation wherein plasmid DNA is partitioned to a top aqueous phase while RNA partitions predominantly to a lower phase, and subsequently isolating the top aqueous phase;
   (d) increasing the temperature of the isolated top aqueous phase to a temperature above the cloud point of the first polymer and below a temperature where plasmid DNA is degraded and subsequently isolating a top aqueous phase so formed; and, optionally,
   (e) performing a chromatography step to recover the plasmid DNA from the isolated top phase of step (d).

2. The method of claim 1, wherein the amount of the first polymer is about 4.5%(w/w) and the amount of the second polymer is about 4.5%(w/w) of the mixture in step (b).

3. The method of claim 1, wherein the aqueous solution that includes plasmid DNA is a cell lysate, and wherein said method further comprises a step for desalting the cell lysate before step (b).

4. The method of claim 1, wherein the contacting according to step (b) involves mixing at room temperature.

5. The method of claim 1, wherein the isolation according to step (c) and/or step (d) is by centrifugation.

6. The method of claim 1, wherein the salt concentration in said composition in step (a) is at least ten times above that of the aqueous solution.

7. The method of claim 2, wherein the salt concentration in said composition in step (a) is at least ten times above that of the aqueous solution.

* * * * *